US005643280A

United States Patent [19]

Del Rio et al.

[11] Patent Number: 5,643,280
[45] Date of Patent: Jul. 1, 1997

[54] INTEGRAL MYRINGOTOMY TUBE AND INSERTER

[75] Inventors: Eddy H. Del Rio, Royal Palm Beach; William E. Anspach, III, Stuart, both of Fla.

[73] Assignee: The Anspach Effort, Inc., Palm Beach Gardens, Fla.

[21] Appl. No.: 568,915

[22] Filed: Dec. 7, 1995

[51] Int. Cl.$^6$ .................................................. A61F 11/00
[52] U.S. Cl. .................................. 606/109; 604/264
[58] Field of Search ............................... 606/108, 109, 606/167, 174, 205–207; 604/264

[56] References Cited

U.S. PATENT DOCUMENTS

| | | | |
|---|---|---|---|
| 3,871,380 | 3/1975 | Heros | 604/264 |
| 3,897,786 | 8/1975 | Garnett et al. | |
| 3,913,584 | 10/1975 | Walchle et al. | |
| 4,473,073 | 9/1984 | Darnell | |
| 4,713,057 | 12/1987 | Huttner et al. | 604/164 |
| 5,053,040 | 10/1991 | Goldsmith, III | 606/109 |
| 5,304,192 | 4/1994 | Crouse | 606/167 |
| 5,308,357 | 5/1994 | Lichtman | 606/205 |
| 5,496,329 | 3/1996 | Reisinger | 604/264 |

Primary Examiner—Robert A. Hafer
Assistant Examiner—Justine Yu
Attorney, Agent, or Firm—Norman Friedland

[57] ABSTRACT

A myringotomy tube with a axial lumen is constructed with an integral cutting tang extending axially from the flange of the grommet for incising the tympanic membrane without the necessity of a scalpel. A disposable inserter is optionally included that frictionally fits the myringotomy tube to the inserter and includes a handle with an ejector mechanism for releasing the myringotomy tube after it is implanted. The handle is injection molded and inexpensive to fabricate so that the inserter is disposable. The method of construction includes the sequence of assembly to allow the grommet to be releasably affixed to the inserter. The surgical method of use of the inserter and grommet allows the grommet to be implanted in a single step eliminating the necessity of a separate incision.

8 Claims, 2 Drawing Sheets

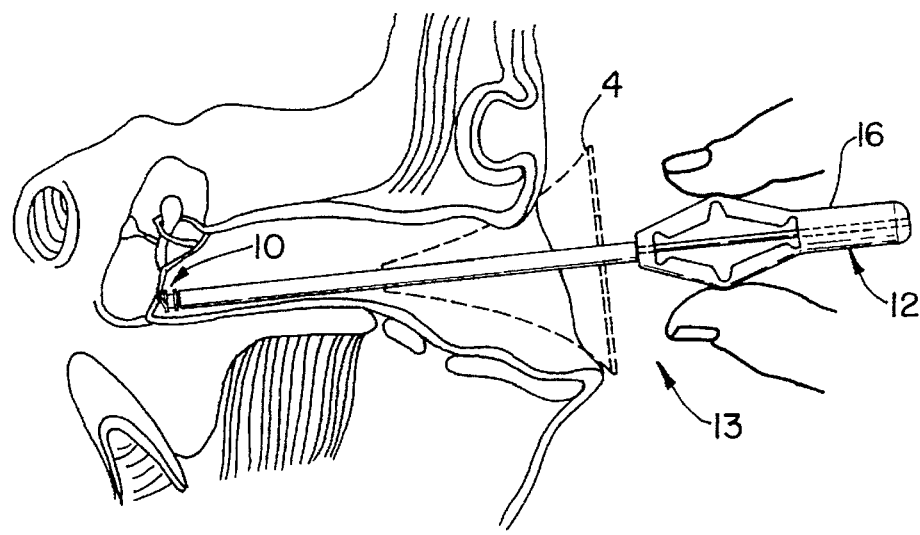
FIG. 1
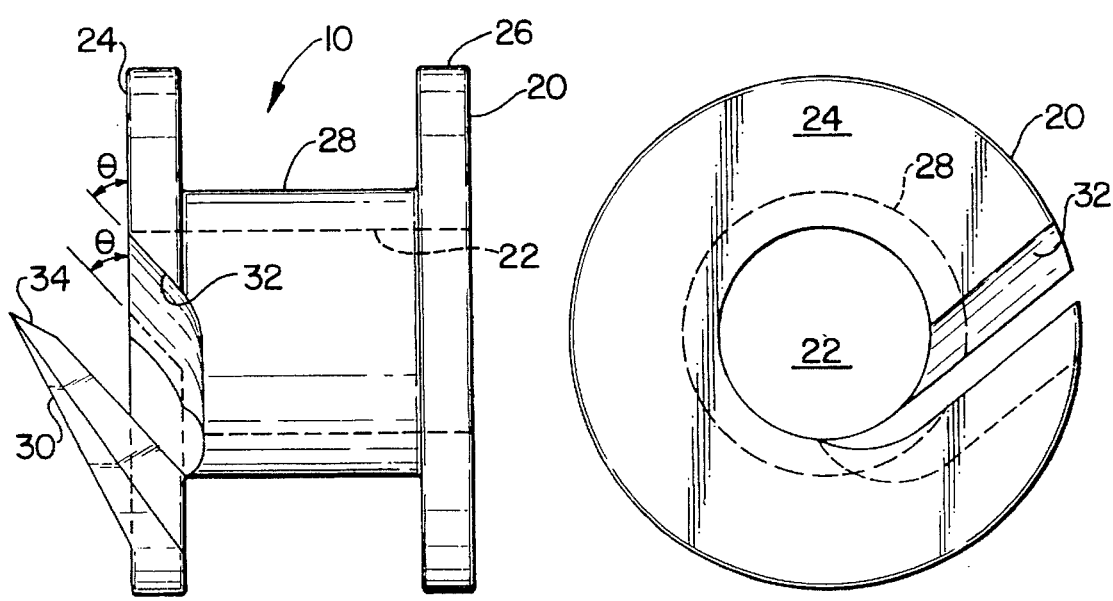
FIG. 2
FIG. 3

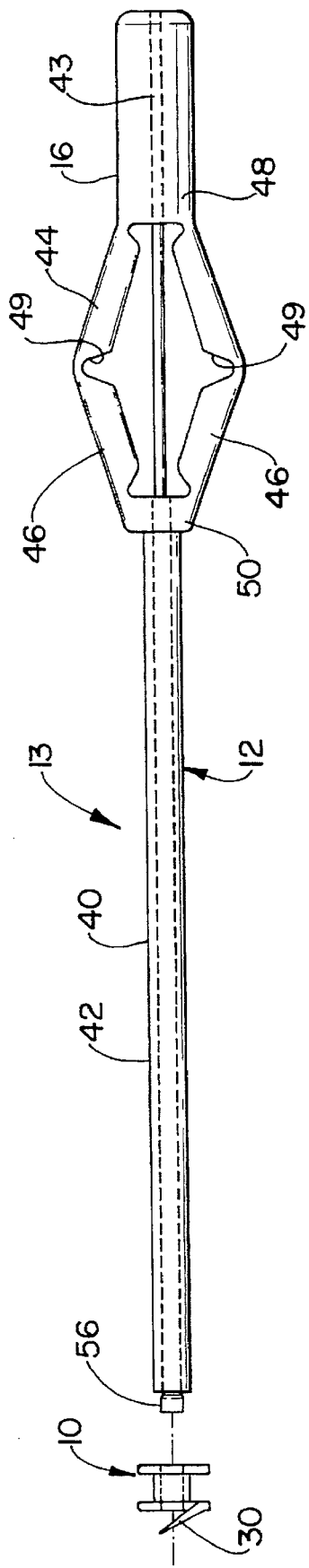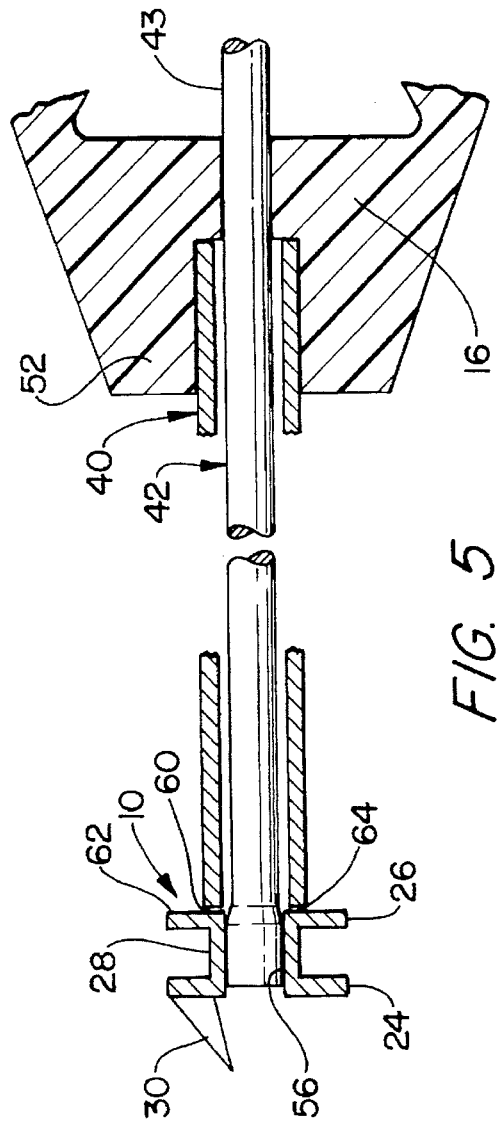

INTEGRAL MYRINGOTOMY TUBE AND INSERTER

TECHNICAL FIELD

This invention relates to ventilating tubes inserted into the tympanic membrane of the ear and particularly to a self-cutting and simultaneous insertion of the ventilating tube and as another embodiment a self-contained grommet and disposable inserter and the methods of use and construction.

BACKGROUND ART

As is well known in the medical technology the surgical procedure for attaching a ventilating tube or grommet (sometimes referred to as a myringotomy tube or tympanotomy tube) into the tympanic membrane is by first making an incision into the membrane with a scalpel and next utilizing a releasing and holding tool or inserter to insert the implant into the incision in the tympanic membrane. Some ventilating tubes require suturing the grommet to the surrounding tissue in order to anchor the tube in place. In modern day technology the incision can be made by utilizing a laser or other cutting apparatus.

There are a number of ventilating tubes commercially available from, for example, Richards Medical Company in Memphis, Tenn. These ventilating tubes include, amongst others, the Shea Parasol, Shah LT, Shepard Grommet, Moretz-Type, and Rock Pediatric.

Listed are a number of patents that are exemplary of the types of ventilating tubes that are well known in the prior art. Amongst these include U.S. Pat. No. 4,094,303 granted to Johnston on Jun. 13, 1978 entitled "Tympanic Membrane Vent" which provides a grommet that is made from a hydrophobic porous material that allows the passage of air and also allows for tissue ingrowth.

U.S. Pat. No. 4,744,792 granted to Sander et al on May 17, 1988 entitled "Middle Ear Ventilating Tube" relates to a grommet type ventilation tube made from suggested biocompatible materials that resist extrusion while attempting to prevent clogging of the ventilation opening.

U.S. Pat. No. 4,695,275 granted to Bruce et al on Sep. 22, 1987 entitled "Middle Ear Ventilation Tube" is another ventilating tube that is made from a flexible material that is collapsible in order to facilitate the insertion of the tube in the slit or opening in the tympanic membrane.

U.S. Pat. No. 4,174,716 granted to Treace on Nov. 20, 1979 entitled "Myringotomy Tube" relates to a ventilating tube that is configured for the ease of insertion in the incision in the tympanic membrane.

U.S. Pat. No. 4,168,697 granted to Cantekin on Sep. 25, 1979 entitled "Middle Ear Ventilating Tube and Method" relates to another ventilating tube that includes a permeable membrane covering the outer end of the lumen formed in the grommet.

In each of the ventilating tubes disclosed in the above-noted references, the ventilating tube is inserted into a pre-cut incision. This procedure is complicated by the fact that the external auditory meatus is a circuitous and narrow passage, which is particularly so in enfants, that require a certain degree of skill to not only make the incision, but also insert the tube into the incision.

The present invention obviates the necessity of the pre-cut incision and simultaneously provides means for securing the ventilating tube to the tympanic membrane. Hence, in accordance with this invention the myringotomy tube simultaneously performs the functions of incising the tympanic membrane and insertion thereof. The cutting tang of the grommet is configured to impart a helical type path into the membrane to anchor the grommet to the membrane and hence, eliminate the necessity of suturing the grommet to the adjacent tissue.

In another embodiment of this invention, the inserter is disposable and is pre-assembled with the grommet which is releasably mounted on the distal end of the inserter so that the inserter/grommet assembly serves as the tool for incising and inserting the grommet in the tympanic membrane and the inserter after releasing the grommet is disposable. The invention contemplates the methods of construction and use of the combined inserter/grommet.

SUMMARY OF THE INVENTION

An object of this invention is to provide an improved myringotomy tube that is self cutting for implantation.

A feature of this invention is to provide a ventilating tube that includes a cutting tang that extends axially from the flange of a grommet. The grommet is characterized as relatively inexpensive to fabricate, ease of installation and the elimination of independent cutting tools that are necessary in surgically slitting the tympanic membrane prior to inserting the implant.

The cutting tang is configured and dimensioned so as to anchor the grommet to the membrane to secure the ventilating tube in place.

Another object of this invention is to provide an improved myringotomy tube/inserter where the inserter is disposable and the myringotomy tube is pre-attached to the inserter. The inserter includes a pull rod with the diameter of the distal end portion thereof being enlarged to accommodate a slight friction fit of the myringotomy tube and a support tube concentrically mounted relative to the pull rod and defining a striking end that forces the myringotomy tube off of the distal end as part of the surgical procedure for the insertion of myringotomy tube. The inserter includes a handle that supports the pull rod and the support tube with a self-contained ejection mechanism so that the slight pressing of ejector mechanism by the fingers of the surgeon axially positions the support tube relative to the pull rod for releasing the myringotomy tube.

The method of fabricating the myringotomy tube and inserter is by the following steps:

1) providing a grommet with axially spaced flanges and a reduced diameter mid portion and a cutting portion formed on one of the flanges.

2) providing an inserter with a handle formed with ejection mechanism, a pull rod with an enlarged diameter portion at the distal end and a support tube concentric to the pull rod, 3) dimensioning the distal end of the enlarged diameter portion of the pull rod and the bore of the grommet to be of substantially the same diameter, 4) press fitting the grommet on the distal end of the pull rod, 5) attaching the support tube to the end of the handle such that the distal end of the support tube is adjacent to the proximal end of the grommet and is concentric relative to the pull rod, 6) providing ejection mechanism on the handle with fingers interconnecting an annular portion at the proximal end of the handle and a moveable annular portion at the distal end of the handle and affixing the pull rod to the proximal end and affixing the support tube to the distal end so that squeezing the fingers of the ejector on the handle forces the support tube to release the grommet from the pull rod.

The method of use of the inserter/myringotomy tube for inserting the myringotomy tube with a self cutting tang into the tympanic membrane of the ear of a patient so the handle of the inserter is external of the ear where the grommet incises the tympanic membrane, and simultaneously inserting the grommet into the incision so that the reduced diameter mid portion thereof anchors the grommet to the membrane, 1) inserting the inserter into the external auditory meatus of the ear of a patient until the cutting edge bears against the tympanic membrane, 2) cutting and simultaneously inserting the grommet into the tympanic membrane with the self-cutting tang by rotating the inserter until the grommet invades the tympanic membrane and the smaller diameter of the grommet is positioned relative to the tympanic membrane for being anchored therein, 3) simultaneously squeezing the handle of the inserter and removing the inserter from the external auditory meatus for releasing the grommet from the inserter.

The foregoing and other features of the present invention will become more apparent from the following description and accompanying drawings.

BRIEF DESCRIPTION OF DRAWINGS

FIG. 1 is a schematic view illustrating the grommet of the combined inserter/self-cutting grommet of this invention being inserted into the tympanic membrane of the ear of a patient;

FIG. 2 is a view in elevation showing the grommet;

FIG. 3 is a side view of FIG. 1;

FIG. 4 is an exploded view in side elevation showing the configuration of the combined grommet/inserter of this invention; and FIG. 5 is a partial view in section showing the details of the combined grommet/inserter of this invention.

DETAILED DESCRIPTION OF THE PREFERRED EMBODIMENT

The terms grommet, ventilation tube, tympanotomy tube and myringotomy tube are used interchangeably throughout the description of the preferred embodiment and are sometimes referred to as an implant for venting and draining the tympanic cavity. While the grommet is shown in the preferred embodiment as being implanted by the use of the disposable inserter of this invention, it is to be understood that the grommet may be implanted by use of other inserters and it is not necessary for the grommet of this invention to be inserted by the inventive inserter described in the preferred embodiment.

Reference is now made to FIG. 1 which schematically shows the grommet of this invention generally indicated by reference numeral 10 and the inserter of this invention generally indicated by reference numeral 12 of the combined grommet/inserter generally indicated by reference numeral 13 of this invention where the grommet 10 is in the process of being implanted into the tympanic membrane. The procedure for accomplishing the implant is by inserting the grommet/inserter assembly 13 into the opening of the funnel shaped guide 14 which is partially inserted into the external auditory meatus of the ear leaving the handle 16 of the grommet/inserter 13 at the exterior of the ear and accessible to the surgeon. The grommet/inserter 13 is pushed axially until the cutting tang 30 bears against and incises the temporal membrane. The surgeon next rotates the grommet/inserter 13 and further incises the membrane until an opening dimensioned slightly smaller than the diameter of the distal flange of the grommet 10 so that the grommet is forced into the membrane by compressing the membrane and continuing the insertion until the membrane is within the reduced diameter mid-portion of grommet 10 and sandwiched between the distal and proximal flanges of the grommet. The membrane that was previously compressed or expanded is allowed to relax and fit into the grommet which thereby is anchored thereto. The surgeon next squeezes the ejector portion of the handle which automatically releases the grommet the pull out the inserter portion of the grommet/inserter 13 as will be described in more detail hereinbelow.

The next portion of this description will describe the inventive grommet 10. As mentioned above and referring to FIGS. 2 and 3, the grommet 10 is self cutting and consists of a cylindrical shaped main body 20 with a central lumen 22, the distal flange 24, the proximal flange 26, the reduced diameter mid-section 28 and the cutting tang 30. Cutting tang 30 is formed integrally with the main body 20 by cutting the inner diameter of the distal flange 24. The location of the slot 32 is Judiciously selected and the dimension of slot 32 is discretely selected by making a substantially 0.010 inch straight through cut starting at the juncture of the lumen 22 and distal flange 24 to the depth of the distal flange 24 with the cutting tool of a milling machine. The angle θ of the slot 32 substantially equal to 45°. This will provide a cutting tang with the required cutting edge will be integrally formed in the grommet. The cutting operation with the use of the milling cutter as described immediately above without any other machining operation forms a cutting edge on tang 30 that is sufficiently sharp to penetrate the tympanic membrane. After the cut is made the tang 30 is bent outwardly and is oriented to lie tangentially relative to the diameters of the mid-section 28 and to the approximate end of distal flange 24. By the Judicious location of slot 32 and the discrete cut thereof, the rotation of the grommet 10 and the cutting edge 34 when being inserted into the tympanic membrane defines a helical path and is rotated by the surgeon until a sufficient opening in the tympanic membrane allows the distal flange 24 to pass therethrough. As mentioned in the above paragraphs the dimension of the cutting tang 30 is such that the incision into the membrane is sufficiently small so that the distal flange is slightly forced through the membrane. The membrane and tissue surrounding the incision is slightly compressed and expanded so that when the membrane aligns within the reduced diameter midsection of the grommet, the membrane and tissue expands therein. It is apparent from the foregoing that this contraction and expansion of the membrane structure serves to anchor the grommet and keeps it from falling out.

In the preferred embodiment the grommet is made from a surgical grade of titanium or its alloy and is sized as follows (it being understood that other materials and sizes could be used):

The diameters and widths of the distal and proximal flanges are substantially 0.100 and 0.010 inch respectively, the diameter of the midsection is substantially 0.055 inch, the diameter of the lumen is substantially 0.040 inch.

The next portion of this invention will describe the inserter 12. Referring next to FIGS. 4 and 5, the inserter 12 consists of handle 16, support tube 40, pull rod 42 and the ejector mechanism 44. The ejector mechanism 44 is comprised of the fingers 46 that are circumferentially spaced around handle 16 that interconnect on one end to the annular proximal portion 48 of handle 16 and on the opposite end to the annular distal portion 50 of handle 16. As is apparent from FIG. 4 squeezing the fingers 46 radially inwardly forces the distal portion 50 to displace axially until the support tube abuts the grommet and the proximate portion 48 moves axially in the opposite direction when the force created by the grommet overcomes the force on the distal portion 50 to pull the pull rod out of the lumen of the grommet.

As best seen in the enlarged partial section of FIG. 5, the proximal end 52 of support tube 40 fits into a central recess 54 formed at the distal end of handle 16 and is affixed thereto. The proximal end 43 of pull rod 42 which is disposed concentrically to support tube 40 fits through a central bore extending from the distal end to the proximal end of handle 16 and passing through the fingers 46 and then is affixed to the annular proximal portion 48 of handle 16. The diameter of the end portion 56 of the distal end of pull rod is increased to be substantially equal to the diameter of the lumen 22 of grommet 10. The purpose of the dimension of the diameter of the end portion 56 is so that when the grommet is assembled to the inserter, the grommet will be slightly forced fitted onto the enlarged diameter portion and the frictional engagement will be sufficient to hold the grommet in place when the surgeon implants the grommet. The connections of the grommet to the pull rod and pull rod to the handle could be splined if the frictional force was not sufficient to withstand the torque of the rotational movement during the incision.

The assembly of the grommet/inserter and the operation of the ejector mechanism 44 is as follows:

The handle and ejector mechanism is made from a suitable plastic or synthetic material such as polyurethane, polyvinylchloride and the like that is ejection molded into a unitary unit. The support rod 40 is first assembled to the handle. The pull rod is next assembled by inserting the small diameter of the pull rod 42 through the distal end of the support tube to the annular portion 48 of handle 16 which may extend through or partially through the handle 16 and is affixed thereto. The enlarged diameter portion 56 of pull rod 42 extends beyond the end of support tube 40 and the grommet 10 is force fitted thereon. As is apparent from the foregoing, the distal end of support tube 40 defines a striking end 60 and is in close proximity to the outer face 62 of the proximal flange 26. To release the grommet 10 the fingers 46 are squeezed by the fingers of the surgeon (see FIG. 1) radially inwardly causing the annular portion 50 to move axially toward the right hand end forcing the support tube to move toward the right and abut the surface portion 64 of face 62. The slots 49 are provided in the fingers to reduce the resistance that the fingers exert relative to the squeezing force. Since grommet 10 is anchored to the tympanic membrane the pull rod is forced to move toward the left direction and out of the lumen. The inserter is then retracted out of the external auditory meatus and may be discarded.

What has been shown by this invention is a grommet that integrally includes the cutting tool to incise the tympanic membrane without the necessity of a scalpel. The procedure for this implant is simpler and less expensive than the heretofore known procedures. The combined grommet/inserter instrument is relatively inexpensive to fabricate making it economically practical to be disposable.

Although this invention has been shown and described with respect to detailed embodiments thereof, it will be appreciated and understood by those skilled in the art that various changes in form and detail thereof may be made without departing from the spirit and scope of the claimed invention.

I claim:

1. An inserter and grommet combination comprising a grommet and an inserter, said inserter is adapted for implanting a grommet with an axial lumen to the tympanic membrane of an ear comprising an elongated support tube having a lumen, a distal end, and a proximal end, a pull rod concentrically disposed relative to said support rod, said pull rod having an enlarged diameter portion extending beyond the distal end of said support tube, said grommet being frictionally supported to said enlarged portion, an ejector handle having a distal end and a proximal end portion, a first annular portion formed on said distal end of the ejector handle and a second annular portion formed on said proximal end portion, finger movable to a radially inward position interconnecting said first annular portion and said second annular portion, said proximal end of said support rod being affixed to said first annular portion, said pull rod being affixed to said second annular portion, said finger means being movable radially inwardly to position said support rod to abut said grommet and pull said pull rod in an axial direction away from said grommet, whereby the rectilinear motion of the push rod and support rod relative to each other implants said grommet in said tympanic membrane.

2. An inserter and grommet combination as claimed in claim 1 wherein said handle is made from a plastic injection molded material.

3. An inserter and grommet combination as claimed in claim 2 wherein said grommet is combined with said inserter to define a grommet/inserter assembly, said pull rod being in sliding relation with said lumen and force fitted thereto, whereby when said grommet is anchored to said tympanic membrane and said finger means are squeezed radially inwardly said support tube abuts said grommet and said pull rod is moved out of said lumen.

4. An inserter and grommet combination as claimed in claim 3 wherein said grommet includes a front face, said support tube having a striking face adapted to bear against said front face, and an inner diameter of said support tube being larger than an outer diameter of said enlarged diameter portion whereby said enlarged diameter portion is allowed to pass into said support tube for retracting said inserter from said grommet.

5. An inserter and grommet combination as claimed in claim 4 wherein said grommet includes a main cylindrical body with a proximal flange, a distal flange and a lumen, a cutting tang extending from the proximal flange and formed integrally therewith.

6. An inserter and grommet combination as claimed in claim 5 wherein said grommet further includes a central axis, said distal flange having a front surface, the cutting tang extending axially from said front surface and a slot angularly disposed in said distal flange relative to the central axis extending from the front surface through said distal flange of said grommet.

7. An inserter and grommet combination as claimed in claim 6 wherein said slot is 45 degrees relative to said central axis.

8. An inserter and grommet combination as claimed in claim 7 wherein said grommet is made from a group of metals consisting of essentially surgical grade titanium or titanium alloy thereof.

* * * * *